(12) United States Patent
Krog

(10) Patent No.: US 6,557,582 B2
(45) Date of Patent: May 6, 2003

(54) FLOW CELL

(75) Inventor: Jens Peter Krog, Ulstrup (DK)

(73) Assignee: Danfoss A/S, Nordborg (DK)

( * ) Notice: Subject to any disclaimer, the term of this patent is extended or adjusted under 35 U.S.C. 154(b) by 0 days.

(21) Appl. No.: 10/014,280

(22) Filed: Dec. 11, 2001

(65) Prior Publication Data

US 2002/0059958 A1 May 23, 2002

Related U.S. Application Data

(63) Continuation of application No. PCT/DK00/00317, filed on Jun. 14, 2000.

(30) Foreign Application Priority Data

Jun. 18, 1999 (DE) .......................... 199 27 850

(51) Int. Cl.$^7$ .............................. F16K 11/24
(52) U.S. Cl. ................... 137/599.03; 137/606
(58) Field of Search ................. 137/597, 606, 137/599.03, 599.04

(56) References Cited

U.S. PATENT DOCUMENTS

| | | |
|---|---|---|
| 2,828,766 A | 4/1958 | Postmus |
| 3,690,833 A | 9/1972 | Ferrari |
| 4,816,083 A * | 3/1989 | Bangyan ................ 137/606 |
| 5,431,185 A | 7/1995 | Shannon et al. |
| 5,590,686 A * | 1/1997 | Prendergast ............ 137/597 |
| 5,599,503 A | 2/1997 | Manz et al. |
| 5,695,719 A | 12/1997 | Lynggaard et al. |

FOREIGN PATENT DOCUMENTS

| | | |
|---|---|---|
| CH | 646 503 | 11/1984 |
| DE | 24 36 113 | 2/1976 |
| DE | 196 48 685 | 6/1997 |
| EP | 0 047 130 | 10/1982 |
| EP | 0 412 046 | 6/1991 |

OTHER PUBLICATIONS

Berg et al., "Miniaturized Chemical Analysis Systems", Proceedings, 1994 $5^{th}$ International Symposium, Oct. 2–4, 1994, pp. 181–184, XP002901273, figs. 1, 6, 7.

* cited by examiner

Primary Examiner—Stephen M. Hepperle
(74) Attorney, Agent, or Firm—Altera Law Group LLC

(57) ABSTRACT

A flow cell having at least two inlet channels, each connectable with a reservoir and controllable via valves and ending in an inlet chamber is disclosed herein. Each of two ends of the inlet chamber is connected with a discharge channel through at least two outlet channels. Previously supplied fluid remaining in the inlet chamber is displaced into the discharge channel by newly supplied fluid. The at least two outlet channels establish fluid purity in the chamber via rapid fluid transfer.

Figure 1:
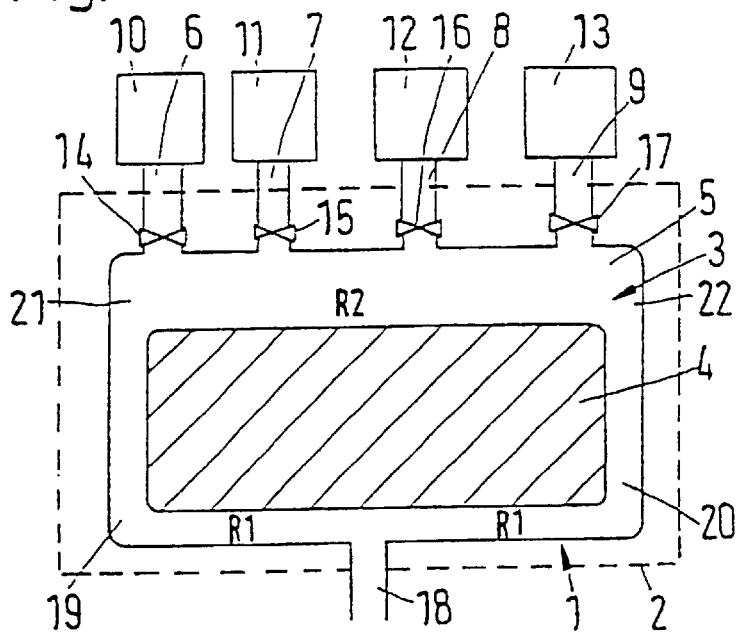

11 Claims, 1 Drawing Sheet

FLOW CELL

This application is a continuation of international application serial number PCT/DK00/00317, filed Jun. 14, 2000.

The invention concerns a flow cell with at least two inlet channels, each connectable with a reservoir and controllable by means of valves and ending in an inlet chamber, and a common discharge channel.

Flow cells of this kind are, for example, known in the shape of micro systems from the chemical analysis technique. This concerns planar micro systems, having substrates of glass, silicium, plastic or the like. These systems are also known under the name "Lab on a chip". They have built-in micro-valves, channels for fluid transport are available, reservoirs for fluid are provided, etc. The channel structure can be produced by etching, milling, boring, die-casting, hot embossing etc.

In this connection it is disadvantageous that the latest transported fluid always remains in the chamber, where it pollutes the next fluid to be transported. Therefore, rather long dead times have to be accepted, before an analysis can be made with the new fluid. Additionally, the first mentioned fluid remains in corners and dead spaces, so that a complete removal is difficult. This is particularly the case, when more than two inlet channels are required.

In an infusion arrangement as shown in U.S. Pat. No. 5,431,185, it is known to add drugs to the infusion solution via three inlet channels being controllable by valves. Pollution cannot take place here, as the continuously incoming infusion solution acts as rinsing fluid.

The invention is based on the task of providing a flow cell as mentioned in the introduction, in which the pollution risk is drastically reduced and the dead time until the new fluid is available in pure condition is substantially reduced.

According to the invention, this task is solved in that each of the two ends of the inlet chamber is connected with the discharge channel via an outlet channel.

New incoming fluid flows to both outlet channels and therefore press all rests of the old fluid via the ends of the inlet chamber and the outlet channels to the discharge channel. The new fluid, no matter from which inlet channel it flows in, is therefore rinsing medium for the old fluid. The dead time until the passing of pure new fluid is short. Inlet chamber and outlet channels can easily be dimensioned so that no dead spaces occur.

It is advantageous that the inlet chamber has a width, which is small in comparison with the length measured between the ends. The new fluid therefore flows closely past the ends of the other inlet channels in the inlet chamber, which gives a good cleaning effect. If possible, the width should be less than ⅕, preferably less than ¹⁄₁₀ of the length.

It is also recommended that the last section of each inlet channel be formed by its valve. The new fluid therefore passes immediately by the closing member, which additionally improves the rinsing effect.

A particularly good effect occurs on a suitable choice of flow resistances of inlet chamber and outlet channels. Thus, it is recommended that the flow resistance of each outlet channel is at least equal to ⅕ of the flow resistance of the inlet chamber between its ends, and preferably at least equal to this flow resistance. In this connection, the flow resistance can be expressed in bar/(l/s), bar indicating the pressure, l the flow quantity and s the time. The desired flow resistances can easily be obtained through a selection of the cross section and the length of the outlet channels.

With regard to design, it is advantageous to have a chamber, which has on one side the inlet channels, on the other side the discharge channel and between these an island-like restriction element, which is limited by the inlet chamber and the two outlet channels. In this connection, the required chambers and channels can be planarly dimensioned, which in relation to three-dimensional embodiments simplifies the production and is particularly interesting to micro systems.

It is advantageous that the chamber and the restriction element are approximately rectangular. Such shapes are easy to produce and can be accurately dimensioned.

It is advantageous that the inlet chamber with the inlet channel ends and the outlet channels are arranged symmetrically to the connection of the discharge channel. This symmetry gives substantially the same conditions on cleaning the chamber by means of the subsequent fluid.

Additionally, it is possible without problems that at least three inlet channels end in the inlet chamber. Therefore, more than two fluids can optionally be available.

Further, it is expedient that the first section of the discharge channel is formed by a micro pump. Thus, the micro flow cell provided with a pump can be kept small.

A preferred opportunity comprises that four micro valves are connected with the inlet chamber. The length of the inlet chamber caused by this can be used for the length of the outlet channels or even for the arrangement of the micro pump and—subsequently—the two outlet channels.

Preferred is the use in a chemical micro analysis system. There are several opportunities to perform different measurings at relatively short intervals. For example, the micro flow cell is suitable for water analyses in sewage plant.

In the following, the invention is explained in detail by means of preferred embodiments in connection with the drawings, showing:

FIG. 1 a schematic view of the micro flow cell according to the invention

Figure 2:
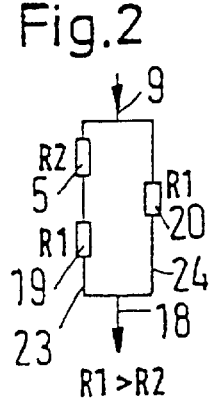

FIG. 2 a belonging circuit diagram

Figure 3:
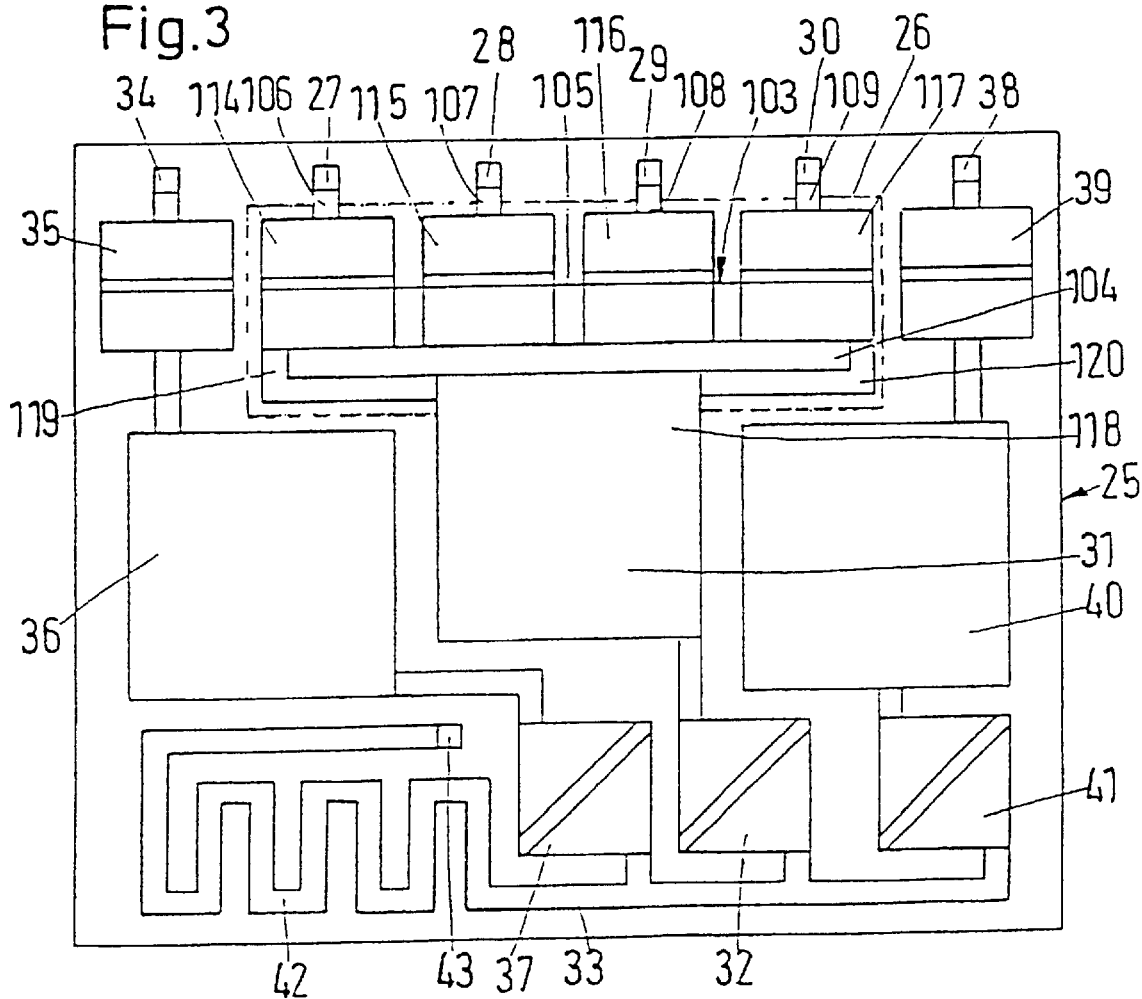

FIG. 3 a micro chip with the micro flow cell according to the invention

A micro flow cell 1 is made on a chip 2 shown with dotted lines. It consists of a substrate of silicium or the like, having on its surface indentations, which are covered by an additional layer, which also contains active elements. An approximately rectangular chamber 3 is available, in which residual material forms an equally, approximately rectangular, island-like restriction element 4. Four inlet channels 6, 7, 8 and 9, each connected with a reservoir 10, 11, 12 and 13 for fluids, end in an inlet chamber 5 of the chamber 3. The last section of each inlet channel is formed by a controllable micro valve 14, 15, 16 and 17. A discharge channel 18 is arranged in the side of the chamber 3 lying opposite the inlet chamber 5. The chamber 3, the inlet channels 6 to 9 and the discharge channel 18 are lying approximately on one level, thereby leading to a planar system.

The restriction element 4 is arranged in the chamber 3 in such a way that beside the inlet chamber 5 two outlet channels 19 and 20 are formed, which extend from the ends 21 and 22 of the inlet chamber 5 to the discharge channel 18.

Each of the two outlet channels 19 and 20 has a flow resistance R1, which is larger than the flow resistance R2 of the inlet chamber 5. Preferably, the flow resistance is a multiple times larger. The endeavoured effects also occur with a smaller flow resistance in the outlet channels. When opening one of the micro valves, for example the micro valve 17, this gives a circuit diagram as shown in FIG. 2. There are two parallel branches 23 and 24 between the end of the inlet channel 9 and the discharge channel 18. The first branch 23 has a flow resistance R1+R2, which is only slightly larger than the flow resistance R1 of the branch 24. Accordingly, the fluid from the inlet channel 9 flows off through both branches, thus displacing the remaining volume from the previous supply of a different fluid still available in the chamber 3. Already after a short while the fluid supplied via the inlet channel 9 flows off in pure form via the discharge channel 18. The same applies for the opening of another micro valve 14, 15 or 16.

FIG. 3 shows on a chip 25 with the approximate dimensions 8×10 mm² a chemical micro analysis system for water analyses in sewage plant. The area 26 surrounded by dotted lines substantially corresponds to the parts of FIG. 1. Therefore, for corresponding parts, reference numbers increased by 100 are used. Also here, there is a chamber 103 with an island-like restriction element 104, so that it is possible to distinguish between an inlet chamber 105 and two outlet channels 119 and 120. The inlet channels 106, 107, 108 and 109 are provided with plug connections 27, 28, 29 and 30, which serve the connection with the reservoirs 10, 11, 12 and 13. The last section of the inlet channels is formed by the micro valves 114, 115, 116 and 117, whose outlet part overlaps the inlet chamber 105. The first section of the discharge channel 118 is formed by a micro pump 31, which overlaps the outlet channels 119, 120. In a manner of speaking, the micro flow cell is used as inlet valve for the micro pump. Also here the advantages explained in connection with the FIGS. 1 and 2 apply.

The discharge channel 118 leads via the micro pump 31 and an additional micro valve 32 to an outlet channel 33, which may receive an additional fluid from a connection 34 via a micro valve 35, a micro pump 36 and a micro valve 37, as well as from a connection 38 via a micro valve 39, a micro pump 40 and a micro valve 41. Subsequently comes a meander-shaped channel 42, in which a mixing can take place and which leads to a connection 43. A light cell arrangement can be connected to said connection 43, with which a photo spectroscopy can be performed.

Thus, for example, the inlet channel 8 can carry a test fluid, the inlet channels 6, 7 and 9 each carrying a reagent. Via the connections 38 and 34 the fluids to be examined can be added. The capacity of such a microanalysis system amounts to approximately 0.1 to 100 micro litres per minute.

Micro valves and micro pumps are known per se. In particular, they can be operated piezoelectrically. However, also other ways of operating are possible, for example by compressed air.

The use of the micro flow cell is not limited to chemical analysis systems. It can be used anywhere, where optionally one or several different fluids must be added, and where a fluid change must only cause short dead times until the supply of the newly added fluid in pure form is established.

The flow cell according to the invention can also be realised in different ways, for example so that the inlet chamber and the outlet channels are made of hoses.

What is claimed is:

1. A flow cell for directing a flow of a fluid comprising:
   at least two inlet channels;
   an inlet chamber connected to the at least two inlet channels;
   at least two outlet channels connected to the inlet chamber;
   a common discharge channel connected to the at least two outlet channels; and
   a restriction element located between the at least two inlet channels and the common discharge channel, wherein the restriction element directs the flow of the fluid from the inlet chamber into the at least two outlet channels and an entire fluid content in the inlet chamber is exchanged substantially unchanged through the at least two outlet channels.

2. The flow cell according to claim 1, wherein the inlet chamber has a width which is small in comparison with a length measured between ends of the inlet chamber.

3. The flow cell according to claim 1, wherein an end section of each inlet channel is formed by a valve.

4. The flow cell according to claim 1, wherein the inlet chamber and restriction element are substantially rectangular shaped.

5. The flow cell according to claim 1, wherein the at least two inlet channels and the at least two outlet channels are symmetrically arranged with respect to the discharge channel.

6. The flow cell according to claim 1, wherein at least three inlet channels end in the inlet chamber.

7. The flow cell according to claim 1, wherein a first section of the discharge channel is formed by a micro pump.

8. The flow cell according to claim 1, wherein four micro valves are connected with the inlet chamber.

9. The flow cell according to claim 1, wherein the flow cell is a component in a chemical microanalysis system.

10. A flow cell for directing a flow of a fluid comprising:
    at least two inlet channels;
    an inlet chamber connected to the at least two inlet channels;
    at least two outlet channels connected to the inlet chamber; and
    a common discharge channel connected to the at least two outlet channels, wherein an entire fluid content in the inlet chamber is exchanged substantially unchanged through the at least two outlet channels and the flow resistance of each of the at least two outlet channels is at least equal to ⅕ of the flow resistance of the inlet chamber between ends thereof.

11. The flow cell according to claim 10, wherein the flow resistance of each of the at least two outlet channels is at least equal to the flow resistance of the inlet chamber between ends thereof.

* * * * *